(12) United States Patent
Hertogs et al.

(10) Patent No.: US 7,494,768 B1
(45) Date of Patent: Feb. 24, 2009

(54) MUTATIONAL PROFILES IN HIV-1 PROTEASE AND REVERSE TRANSCRIPTASE CORRELATED WITH PHENOTYPIC DRUG RESISTANCE

(75) Inventors: Kurt Hertogs, Antwerp (BE); Brendan Larder, Churchlane (GB); Rudi Pauwels, Bonheiden (BE)

(73) Assignee: Tibotec-Virco Virology BVBA, Mechelen (BE)

( * ) Notice: Subject to any disclaimer, the term of this patent is extended or adjusted under 35 U.S.C. 154(b) by 0 days.

(21) Appl. No.: 09/580,491

(22) Filed: May 30, 2000

Related U.S. Application Data

(60) Provisional application No. 60/136,743, filed on May 28, 1999.

(51) Int. Cl.
*C12Q 1/70* (2006.01)
*C12Q 1/68* (2006.01)
*C12P 19/34* (2006.01)

(52) U.S. Cl. .................. 435/5; 435/6; 435/29; 435/911; 435/912; 436/63; 436/501; 436/601

(58) Field of Classification Search ................ 435/69.1, 435/6; 702/19, 27
See application file for complete search history.

(56) References Cited

U.S. PATENT DOCUMENTS

| 5,631,128 A | 5/1997 | Kozal et al. |
| 5,650,268 A | 7/1997 | Kozal et al. |
| 5,856,086 A | 1/1999 | Kozal et al. |
| 6,221,578 B1 * | 4/2001 | de Bethune et al. ............ 435/5 |

FOREIGN PATENT DOCUMENTS

| WO | WO 97/27480 | 7/1997 |
| WO | WO 99/61658 | 12/1999 |
| WO | WO 99/61666 | 12/1999 |
| WO | WO 99/67427 | 12/1999 |
| WO | WO 00/78996 A1 | 12/2000 |

OTHER PUBLICATIONS

Jon H. Condra et al., Genetic Correlates of In Vivo Viral Resistance to Indinavir, a Human Immunodeficiency Virus Type 1 Protease Inhibitor, Journal of Virology, Dec. 1996, p. 8270-8276.*
Seki et al. Antiviral Chemistry & Chemotherapy (1995), 6(2), 73-9.*
Bakhanashvili et al. Febs Letters (1996), 391(3), 257-262.*
Larder et al. Abstr. Intersci Conf Antimicrob agents Chemother, Sep. 24, 1998; 38:28 (abstract No. LB-4).*
Balotta et al., "Prevalence of Transmitted Nucleoside Analogue-Resistant HIV-1 Strains and Pre-Existing Mutations in *pol* Reverse Transcriptase and Protease Region: Outcome After Treatment in Recently Infected Individuals," *Antiviral Therapy*, 5, pp. 7-14 (2000).
Been-Tiktak et al., "In-Vitro Selection of HIV-1 Variants Resistant to Non-Nucleoside Reverse Transcriptase Inhibitors in Monocyte-Derived Macrophages," *Journal of Antimicrobial Chemotherapy*, 40, pp. 847-853 (1997).

Catucci et al., "Development and Significance of the HIV-1 Reverse Transcriptase M184V Mutation During Combination Therapy with Lamivudine, Zidovudine, and Protease Inhibitors," *Journal of Acquired Immune Deficiency Syndromes*, 21, pp. 203-208 (1999).
Coakley et al., "Phenotypic and Genotypic Resistance Patterns of HIV-1 Isolates Derived from Individuals Treated with Didanosine and Stavudine," *AIDS*, 14, pp. F9-F15 (2000).
Descamps et al., "Susceptibility of Human Immunodeficiency Virus Type 1 Group O Isolates to Antiretroviral Agents: In Vitro Phenotypic and Genotypic Analyses," *Journal of Virology*, pp. 8893-8898 (1997).
Edelstein et al., "Oligonucleotide Ligation Assay for Detecting Mutations in the Human Immunodeficiency Virus Type 1 *pol* Gene That are Associated with Resistance to Zidovudine, Didanosine, and Lamivudine," *Journal of Clinical Microbiology*, pp. 569-572 (1998).
Gunthard et al., "Human Immunodeficiency Virus Replication and Genotypic Resistance in Blood and Lymph Nodes After a Year of Potent Antiretroviral Therapy," *Journal of Virology*, pp. 2422-2428 (1998).
Holodniy et al., "Human Immunodeficiency Virus Reverse Transcriptase Codon 215 Mutations Diminish Virologic Response to Didanosine-Zidovudine Therapy in Subjects with Non-Syncytium-Inducing Phenotype," *The Journal of Infectious Diseases*, 174, pp. 854-857 (1996).
Hsu et al., Higher Fidelity of RNA-Dependent DNA Mispair Extension by M184V Drug-Resistant Than Wild-Type Reverse Transcriptase of Human Immunodeficiency Virus Type 1, *Nucleic Acids Research*, 25(22), pp. 4532-4536 (1997).
Ives et al., "Emergence of Resistant Variants of HIV *in vitro* During Monotherapy with the Proteinase Inhibitor Saquinavir," *Journal of Antimicrobial Chemotherapy*, 39, pp. 771-779 (1997).
Kellam et al., Fifth Mutation in Human Immunodeficiency Virus Type 1 Reverse Transcriptase Contributes to the Development of High-Level Resistance to Zidovudine, *Proc. Natl. Acad. Sci. USA*, 89, pp. 1934-1938 (1992).
Kemp et al., "A Novel Polymorphism at Codon 333 of Human Immunodeficiency Virus Type 1 Reverse Transcriptase Can Facilitate Dual Resistance to Zidovudine and L-2', 3'-Dideoxy-3'-Thiacytidine," *Journal of Virology*, 72, pp. 5093-5098 (1998).
Larder et al., "Tipranavir Inhibits Broadly Protease Inhibitor-Resistant HIV-1 Clinical Samples," *AIDS*, 14, pp. 1943-1948 (2000).
Mohamed et al. "The Sequential Occurrence of *pol* 215 and *pol* 41 Zidovudine Resistance Mutations is Associated in an Additive Fashion with Low CD4 Cell Counts and High Plasma and Cellular HIV Viral Load," *Antiviral Research*, 39, pp. 47-53 (1998).
Moyle, "Viral resistance Patterns Selected by Antiretroviral Drugs and Their Potential to Guide Treatment Choice," *Exp. Opin. Invest. Drugs*, 6(8), pp. 943-964 (1997).

(Continued)

*Primary Examiner*—Michael Borin
(74) *Attorney, Agent, or Firm*—Yunling Ren

(57) ABSTRACT

The invention provides novel mutations, mutation combinations or mutational profiles of HIV-1 reverse transcriptase and/or protease genes correlated with phenotypic resistance to HIV drugs. More particularly, the present invention relates to the use of genotypic characterization of a target population of HIV and the subsequent correlation of this information to phenotypic interpretation in order to correlate virus mutational profiles with drug resistance. The invention also relates to methods of utilizing the mutational profiles of the invention in databases, drug development, i.e., drug design, and drug modification, therapy and treatment design, clinical management and diagnostic analysis.

1 Claim, 3 Drawing Sheets

OTHER PUBLICATIONS

Nakano et al., Clonal Selection of HIV Type 1 Variants Associated with Resistance to Foscarnet *in Vitro*: Confirmation by Molecular Evolutionary Analysis, *Aids Research and Human Rerovirus*, 13(7), pp. 563-573 (1997).

Schmidt et al., "Simple Algorithm Derived from a Geno-/Phenotypic Database to Predict HIV-1 Protease Inhibitor Resistance," *AIDS*, 14, pp. 1731-1738 (2000).

Shafer et al., "Human Immunodeficiency Virus Reverse Transcriptase and Protease Sequence Database," *Nucleic Acids Research*, 28(1), pp. 346-348 (2000).

Tamalet et al., "Multidrug Resistance Genotypes (Insertions in the β3-β4 Finger Subdomain and MDR Mutations) of HIV-1 Reverse Transcriptase from Extensively Treated Patients: Incidence and Association with Other Resistance Mutations," *Virology*, 270, 310-316 (2000).

Villahermosa et al., "Evaluation of Mixtures of Wild-Type HIV-1 and HIV-1 with Resistance Point Mutations Against Reverse Transcriptase Inhibitors," *Antiviral Therapy*, 3, pp. 221-227 (1998).

Wegner et al., "Prevalence of Genotypic and Phenotypic Resistance to Anti-Retroviral Drugs in a Cohort of Therapy-Naïve HIV-1 Infected US Military Personnel," *AIDS*, 14, pp. 1009-1015 (2000).

Angarano et al., "Genotype and Phenotype Resistance: An Overview," *Journal of Biological Regulators and Homeostatic Agents*, 14, pp. 11-14 (2000).

Anton et al., "Comparative Patterns of HIV-1 Genotypic Resistance Profiles in Gut and Plasma," 3rd *Int'l Workshop on HIV Drug Resistance and Treatment Strategies*, Abstract 86, vol. 4, Supp. 1 (1999).

Bethune et al., "Does Natural or Acquired Resistance to Reverse Transcriptase and Protease Inhibitors, Observed in HIV-1 Groups M (Subtypes A-H) and O, Differ from Subtype B," 3rd *Int'l Workshop on HIV Drug Resistance and Treatment Strategies*, Abstract 49, vol. 4, Supp. 1 (1999).

Bloor et al., "Lamivudine-Resistant HIV-1 Clinical Isolates Lacking the MEt184Val Mutation have Novel Polymorphisms in RT," 3rd *Int'l Workshop on HIV Drug Resistance and Treatment Strategies*, Abstract 25, vol. 4, Supp. 1 (1999).

Casado et al., "Rate of Non-nucleoside Reverse Transcriptase Inhibitor Resistance Among Patients Failing a Nevirapine Plus Protease Inhibitor-Containing Regimen," 3rd *Int'l Workshop on HIV Drug Resistance and Treatment Strategies*, Abstract 114, vol. 1, Supp. 1 (1999).

Calvez, V., "Resistance to Antiretroviral Drugs," *Antiviral Therapy*, 3(4), pp. 5-7 (1998).

Chen et al., "Drug Resistance Mutations as Predictors of Phenotypic Zidovudine Resistance in HIV-1 infection," *AIDS*, 11(12), pp. 1528-1529 (1997).

Condra et al., Genotypic or Phenotypic Susceptibility Testing May not Predict Clinical Responses to Indinavir, *Antiviral Therapy*, 1st International Workshop HIV Resistant Treatment Strategies and Eradication, Abstracts 47, pp. 48-49 (1997).

Condra, Jon H., "Resisting Resistance: Maximizing the Durability of Antiretroviral Therapy," *Annals of Internal Medicine*, 128 (11) pp. 951-955 (1998).

D'Aquila, R.T., "HIV-1 Chemotherapy and Drug Resistance," *Clin. Diagnost. Virol*, 3, 299-3166 (1995).

Deeks et al., "Novel Four-Drug Salvage Treatment Regimens After Failure of a Human Immunodeficiency Virus Type 1 Protease Inhibitor-Containing Regimen: Antiviral Activity and Correlation of Baseline Phenotypic Drug Susceptibility with Virologic Outcome," *The Journal of Infectious Disease*,, 179, pp. 1375-1381(1999).

Deeks et al., 2nd *Int'l Workshop on HIV Drug Resistance and Treatment Strategies*, Lake Maggiore, Italy Abstr. 53 (1998).

Eastman et al., "Comparison of Selective Polymerase Chain Reaction Primers and Differential Probe Hybridization of Polymerase Chain Reaction Products for Determination of Relative Amounts of Codon 215 Mutant and Wild-Type HIV-1 Populations," *J. Acq. Imm. Def. Syndr. Human Retrovirol.*, 9, 264-273 (1995).

Eastman et al., "Nonisotopic Hybridization Assay for Determination of Relative Amounts of Genotypic Human Immunodeficiency Virus Type 1 Zidovudine resistance," *J. Clin. Micro.*, 33, 2777-2780 (1995).

Esté et al., "HIV Phenotype & Genotype Data Highlights," 2nd International Workshop on HIV Drug Resistance and Treatment Strategies, Lake Maggiore, Italy (1998).

Fodor et al., "Multiplexed Biochemical Assays with Biological Chips," *Nature*, 364, 555-556 (1993).

Gianotti et al., "Study on Mutations and Antiretroviral Therapy (SMART): Preliminary Results," *Antiviral Therapy*, 4(3), pp. 65-69 (1999).

Gianotti et al., "The Rationale for a Study on HIV-1 Reverse Transcriptase Mutations and Outcome of Antiretroviral Therapy with Two Nucleoside Analogs," *Journal of Biological Regulators and Homeostatic Agents*, pp. 158-162 (1999).

Gingeras et al., "Use of Self-Sustained Sequence Replication Amplification Reaction to Analyze and Detect Mutations in Zidovudine-Resistant Human Immunodeficiency Virus," *The Journal of Infectious Disease*, 164, 1066-1074 (1991).

Hammer et al., "Relationship of Phenotyic and Genotypic Resistance Profiles to Virological Outcome in a Trial of Abacavir, Nelfinavir, Efavirenz and Adefovir Dipivoxil in Patients with Virological Failure Receiving Indinavir," 3rd *Int'l workshop on HIV Drug Resistance and Treatment Strategies*, Abstract 64, vol. 4, Supp. 1 (1999).

Harada et al., "Infection of HTLV-III/LAV in HTLV-1-Carrying Cells MT-2 and MT-4 and Application in a Plaque Assay," *Science*, 229, pp. 563-566 (1985).

Harrigan et al., "Drug Resistance and Short Term Virological Response in Patients Prescribed Multidrug Rescue Therapy," 3rd *Int'l Workshop on HIV Drug Resistance and Treatment Strategies*, Abstract 62, vol. 4, Supp. 1 (1999).

Hertogs et al.,. "Comprehensive HIV Drug Resistance Monitoring Using Rapid, High-Thoughput Phenotypic and Genotypic Assays with Correlative Data Analysis," *Int'l Congress on Drug Therapy in HIV Infection*, Abstracts OP3.4, vol. 12, Supp. 4 (1998).

Hertogs et al., "A Rapid Method of Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Agents Chemother.*, 42, 269-276 (1998).

Hertogs et al., "A Blinded Comparative Analysis of Two Genotyping Service Laboratories: Full Sequence Analysis of HIV-1 Protease and Reverse Transcriptase," 3rd *Int'l Workshop on HIV Drug Resistance and Treatment Strategies*, Abstract 87, vol. 4, Supp. 1(1999).

Hertogs et al., "Common, Rare and New Genotypic and/or Phenotypic HIV-1 Resistance Profiles Observed in Routine Clinical Practice: A Survey of Over 5000 Isolates," 3rd *Int'l Workshop on HIV Drug Resistance and Treatment Strategies*, Abstract 108, vol. 4, Supp 1 (1999).

Hertogs et al., "Testing for HIV-1 Drug Resistance: New Developments and Clinical Implications," *Recent Res. Dev. Antimicrob. Agents Chemother.*, 3(Pt. 1), 83-104. (1999).

Hertogs et al., "A Novel Human Immunodeficiency Virus Type 1 Reverse Transcriptase Mutational Pattern Confers Phenotypic Lamivudine Resistance in the Absence of Mutation 184V," *Antimicrob. Agents Chemother.*, 44(3), 568-573 (2000).

Hirsch et al., "Antiretroviral Drug Resistance Testing in Adults With HIV Infection," *Jama*, 279(24), pp. 1984-1991 (1998).

Holodniy et al., "Determination of Human Immunodeficiency Virus RNA in Plasma and Cellular Viral DNA Genotypic Zidovudine Resistance and Viral Load During Zidovudine-Didanosine Combination Therapy," *Journal of Virology.*, 69, 3510-3516 (1995).

Jopour et al., "Standardized Peripheral Blood Mononuclear Cell Culture Assay for Determination of Drug Susceptibilities of Clinical Human Immunodeficiency Virus Type 1 Isolates," *Antimicrob. Agents Chemother.*, 37, 1095-1101 (1993).

Kellam et al., "Recombinant Virus Assay: A Rapid, Phenotypic Assay for Assessment of Drug Susceptibility of Human Immunodeficiency Virus Type 1 Isolates," *Antimicrobial Agents and Chemotherapy*, pp. 23-30 (1994).

Kempf et al., "Analysis of Virological Response to ABT-378/ Ritonavir Therapy in Protease Inhibitor-Experienced Patients with Respect to Baseline Viral Phenotype and Genotype," 3rd *Int'l Workshop on HIV Drug Resistance and Treatment Strategies*, Abstract 8, Vo. 4, Supp. 1 (1999).

Kemp et al., "Analysis of 5000 HIV-1 Clinical Samples Reveals Complex Non-nucleoside RT Inhibitor Resistance Patterns," 3rd *Int'l Workshop on HIV Drug Resistance and Treatment Strategies*, Abstract 26, vol. 4, Supp. 1 (1999).

Kuritzkes, Daniel R., "HIV Resistance to Current Therapies," *Antiviral Therapy*, 2(3), pp. 61-67 (1997).

Kusimi et al., "Human Immunodeficiency Virus Type 1 Envelope Gene Structure and Diversity In Vivo and after Cultivation In Vivo," *J. Virol.*, 66, 875-885 (1992).

Larder et al., "A Complete Survey, in Over 1,500 Clinical HIV-1 Isolates, of Phenotypic and Genotypic Protease Inhibitor Resistance Profiles (Including Gag Cleavage Site Sequences) and Their Relation to Therapy History," *Int'l Congress on Drug Therapy in HIV Infection*, Abstracts OP3.5, vol. 12, Supp. 4 (1998).

Larder et al., "A Family of Insertion Mutations Between Codons 67 and 70 of Human Immunodeficiency Virus Type 1 Reverse Transcriptase Confer Multinucleoside Analog Resistance," *Antimicrob. Agents Chemother.*, 43(8), 1961-1967 (1999).

Larder et al., "Tipranavir is Active Against a Large Selection of Highly Protease Inhibitor-Resistant HIV-1 Clinical Samples," 3rd *Int'l Workshop on HIV Drug Resistance and Treatment Strategies*, Abstract 5, vol. 4, Supp. 1 (1999).

Larder et al., "HIV with Reduced Sensivity to Zidovudine (AZT) Isolated During Prolonged Therapy," *Science*, 243, 1731-1734 (1989).

Larder, et al., "Predicting HIV-1 Phenotypic Resistance from Genotype Using a Large Phenotype-Genotype Relational Database," 3rd *Int'l Workshop on HIV Drug Resistance and Treatment Strategies*, Abstract 59, vol. 4, Supp. 1 (1999).

Larder et al., "Zidovudine Resistance Predicted by Direct Detection of Mutations in DNA from HIV-Infected Lymphocytes," *AIDS*, 5, 137-144 (1991).

Leigh-Brown et al., "Associations Between Amino Acids in the Evolution of HIV Type 1 Protease Sequences Under Indinavir Therapy," *AIDS Research and Human Retroviruses*, 15(3), pp. 247-253 (1999).

Lennerstrand et al., "Mechanism of Zidovudine and Stavudine Resistance for HIV-1 RT with Amino Acid Insertions Between Codons 68 and 70," 3rd *Int'l Workshop on HIV Drug Resistance and Treatment Strategies*, Abstract 32, vol. 4, Supp. 1 (1999).

Leriche-Guerin et al., "Correlation Between Antiretroviral Resistance Mutations, Biological Parameters, and Clinical Evolution in Zidovudine-Treated Patients Infected with Human Immunodeficiency Virus Type 1," *Eur. J. Clin. Microbiol. Infect. Dis.*, 16, pp. 660-668 (1997).

Lorenzi et al., "Impact of Drug Resistance Mutations on Virologic Response to Salvage Therapy," *AIDS*, 13, pp. F17-F21 (1999).

Miller et al., "Phenotypic Susceptibility to Adefovir Dipivoxil in Clinical Samples with Defined RT Genotypic Resistance Patterns," 3rd *Int'l Workshop on HIV Drug Resistance and Treatment Strategies*, Abstract 40, vol. 4, Supp. 1 (1999).

Miller et al., "Correlates of Resistance to Individual Nucleoside Drugs in Patients who Have Never Taken Them," 3rd *Int'l Workshop on HIV Drug Resistance and Treatment Strategies*, Abstract 41, vol. 4, Supp. 1 (1999).

Miller et al., "Prevalence of Baseline Drug Resistance Mutations in Primary HIV Infection Patients from the Quest Study," 3rd *Int'l Workshop on HIV Drug Resistance and Treatment Strategies*, Abstract 141, vol. 4, Supp. 1 (1999).

Moyle, G., "Current Knowledge of HIV-1 Reverse Transcriptase Mutations Selected During Nucleoside Analogue Therapy: The Potential to Use Resistance Data to Guide Clinical Decisions," *Journal of Antimicrobial Chemotherapy*, 40, pp. 765-777 (1997).

Pauwels et al., 2nd *Workshop on HIV Drug Resistance and Treatment Strategies*, Lake Maggiore, Italy, Abstr. 51 (1998).

Pauwels et al., "Rapid and Automated Tetrazolium-based Colorimetric Assay for the Detection of Anti-HIV Compounds," *J. Virol Methods*, 20, 309-321 (1998).

Perez-Olmeda et al., "Usefulness of Genotypic Analysis of Resistance to Nucleoside Analogues in the Clinical Setting," *Eur. J. Clin. Microbrial Infect. Dis.*, 18, pp. 448-449 (1999).

Piketty et al., "Efficacy of a Five-Drug Combination Including Ritonavir, Saquinavir and Efavirenz in Patients Who Failed on a Conventional Triple-Drug Regimen: Phenotypic Resistance to Protease Inhibitors Predicts Outcome of Therapy," *AIDS*, 13, pp. F71-F77 (1999).

Ren et al., "Crystal Structures of HIV-1 RT Inhibitor Complexes-:'Second Generation' NNRTIs, Efavirenz and S-1153 (AG1549), and NNRTI-and NRTI-resistant Mutant Forms," 3rd *Int'l Workshop on HIV Drug Resistance and Treatment Strategies*, Abstract 20, vol. 4, Supp. 1 (1999).

Richman et al., "Detection of Mutations Associated with Zidovudine Resistance in Human Immunodeficiency Virus by Use of the Polymerase Chain Reaction," *The Journal of Infectious Disease*, 164, 1075-1081 (1991).

Schapiro et al., "Clinical Cross-Resistance Between the HIV-1 Protease Inhibitors Saquinavir and Indinavir and Correlations with Genotypic Mutations," *AIDS*, 13, pp. 359-365 (1999).

Schinazi et al., "Mutations in Retroviral Genes Associated with Drug Resistance," *Int. Antiviral News*, 5, 129-142 (1997).

Schmit et al., "Recent Advances in Antiretroviral Therapy and HIV Infection Monitoring," *Intervirology*, 40, pp. 304-321 (1997).

Stuyver et al., "Line Probe Assay for Rapid Detection of Drug-Selected Mutations in the Human Immunodeficiency Virus Type 1 Reverse Transcriptase Gene," *Antimicrob. Agents Chemotherap.*, 41, 284-291 (1997).

Vella, S., Advances in the Virology of HIV Infection and Implications for Clinical Management, *Aids Clinical Care*, 10(3), pp. 17-19 (1998).

Vingerhoets et al., "The Accuracy and Reproruciblity of High Throughput Genotypic and Phenotypic HIV-1 Resistance Testing Under EN45001 and CLIA Accreditation Labels," 3rd *Int'l Workshop on HIV Drug Resistance and Treatment Strategies*, Abstract 77, vol. 4, Supp. 1 (1999).

Verbiest et al., An Epidemiological Prospective Survey Assessing the Prevalence of HIV-1 Drug Resistance in 230 HIV-1-Positive Antiretroviral-Naive Patients from the USA, 3rd *Int'l Workshop on HIV Drug Resistance and Treatment Strategies*, Abstract 122, vol. 4, Supp. 1 (1999).

Walter et al., "Rapid, Phenotypic HIV-1 Drug Sensitivity Assay for Protease and Reverse Transcriptase Inhibitors," *Journal of Clinical Virology*, 13, pp. 71-80 (1999).

Weber et al., "Molecular Mechanics Analysis of Drug-Resistant Mutants of HIV Protease," *Protein Engineering*, 12(6), pp. 469-474 (1999).

Wegner et al., "The Potential Role of Resistance Testing and Therapeutic Drug Monitoring in the Optimization of Antiretroviral Drug Therapy," 3rd *Int'l Workshop on HIV Drug Resistance and Treatment Strategies*, Abstract 112, vol. 1. Supp. 1 (1999).

Wegner et al., "High Frequency of Antiretroviral Drug Resistance in HIV-1 From Recently Infected Therapy-Naive Individuals," 3rd *Int'l Workshop on HIV Drug Resistance and Treatment Strategies*, Abstract 119, Vol. 4, Supp. 1 (1999).

Winters et al., "Human Immunodeficiency Virus Type 1 Reverse Transcriptase Genotype and Drug Susceptibility Changes in Infected Individuals Receiving Dideoxyinosine Monotherapy for 1 to 2 Years," *Antimicrohbial Agents and Chemotherapy*, pp. 757-762 (1997).

Yahl et al., "Mutation Patterns of the Reverse Transcriptase and Protease Genes in Human Immunodeficiency Virus Type 1-Infected Patients Undergoing Combination Therapy: Survey of 787 Sequences," *Journal of Clinical Microbiology*, pp. 4099-4106 (1999).

Zolopa et al., "A Comparision of Phenotypic, Genotypic and Clinical/Treatment History Predictors of Virological Response to Saquinavir/Ritonavir Salvage Therapy in a Clinic-based Cohort," 3rd *Int'l Workshop on HIV Drug Resistance and Treatment Strategies*, Abstract 68, vol. 4, Supp. 1, 1997).

Zolopa et al., "HIV-1 Genotypic Resistance Patterns Predict Response to Saquinavir—Ritonavir Therapy in Patients in Whom Previous Protease Inhibitor Therapy had Failed," *Ann Intern Med.*, 131, pp. 813-821 (1999).

* cited by examiner

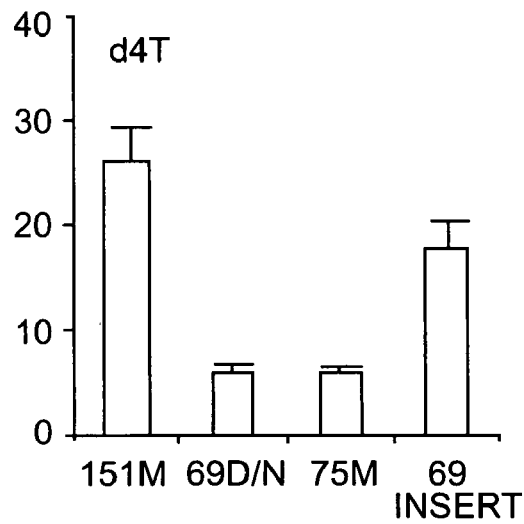
FIG. 2a
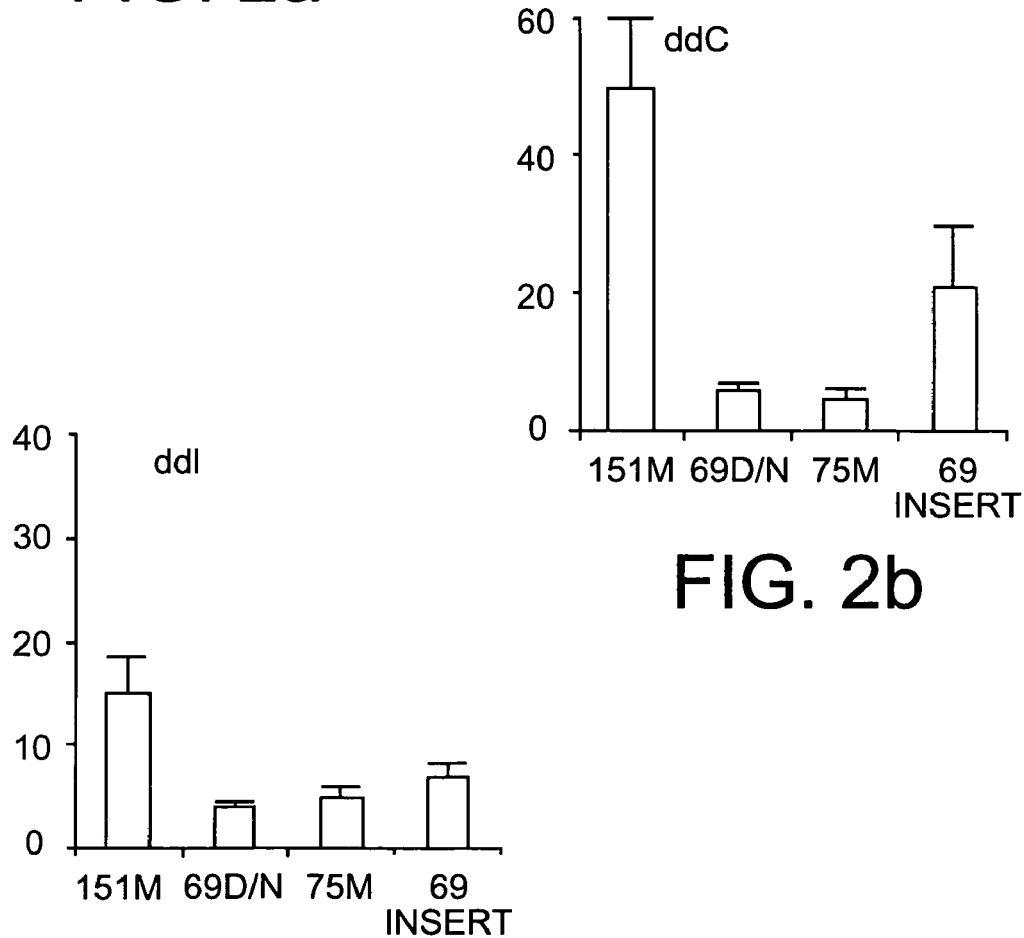
FIG. 2b
FIG. 2c

MUTATIONAL PROFILES IN HIV-1 PROTEASE AND REVERSE TRANSCRIPTASE CORRELATED WITH PHENOTYPIC DRUG RESISTANCE

This application claims the benefit of U.S. provisional application No. 60/136,743, filed May 28, 1999, which is hereby incorporated by reference in its entirety.

The present invention is directed to the field of nucleic acid diagnostics and the identification of base variation in target nucleic acid sequences. More particularly, the present invention relates to the use of such genotypic characterization of a target population of HIV and the subsequent association, i.e., correlation, of this information to phenotypic interpretation in order to correlate virus mutational profiles with drug resistance. The invention also relates to methods of utilizing the mutational profiles of the invention in drug development, i.e., drug design, drug modification, and drug development, therapy and treatment design, clinical management and diagnostic analysis.

The main target cell for HIV infection was identified as the CD4+ subset of T-cells. In order to replicate, HIV first interacts with cells expressing the CD4 surface protein and co-receptor via binding through the gp120 envelope protein. Following fusion via the gp4I domain of the envelope, entry is achieved, the viral particle degraded and the RNA genome transcribed into double-stranded complementary DNA (cDNA). This genetic material is transported into the cell nucleus as part of the pre-integration complex, where the DNA is processed by viral integrase and incorporated into the host genome. In an activated cell, the viral genome is transcribed and subsequently translated into structural proteins and enzyme precursors. The polyproteins, Gag and Gag-Pol containing matrix, capsid, nucleocapsid as well as the enzymes reverse transcriptase, protease and integrase are directed to the cell membrane where proteolytic cleavage by viral protease and virion packaging occurs.

Most of these events have been extensively studied and a number of stages for possible intervention to prevent viral replication have been identified. These include attachment and entry into the host cell, formation of proviral DNA by reverse transcriptase enzymes, integration of proviral DNA into the host cell chromosomes by integrase, as well as virus assembly, including cleavage of the precursor viral proteins, by viral protease. Clinically relevant agents have been developed against two of these target stages—reverse transcription (reverse transcriptase inhibitors (RTI)) and viral assembly (protease inhibitors (PI)).

Retroviral inhibitors may block viral replication in various ways. For example, Nucleoside Reverse Transcriptase Inhibitors (NRTIs), compete with the natural nucleoside triphosphates for incorporation into elongating viral DNA by reverse transcriptase. Chemical modifications that distinguish these compounds from natural nucleosides result in DNA chain termination events. NRTIs that are currently available include zidovudine (ZDV), didanosine (ddI), zalcitabine (ddC), stavudine (d4T), lamivudine (3TC) and abacavir (ABC).

Nucleotide reverse transcriptase inhibitors (NtRTIs) have the same mode of action as NRTIs, but they differ in that they are already monophosphorylated and therefore they require fewer metabolic steps. Adefovir (bis-POM-PMEA) and bis-POC PMPA belong to this category of treatments.

Non-Nucleoside Reverse Transcriptase inhibitor (NNRTIs) are a group of structurally diverse compounds which inhibit HIV reverse transcriptase by noncompetitive binding to or close to the active site of the viral reverse transcriptase enzyme, thereby inhibiting its activity. Available compounds in this group include nevirapine (NVP), delavirdine (DLV) and efavirenz.

Protease Inhibitors (PIs) are peptidomimetic and bind to the active site of the viral protease enzyme, thereby inhibiting the cleavage of precursor polyproteins necessary to produce the structural and enzymatic components of infectious virions. PIs that are currently available include saquinavir (SQV), ritonavir (RTV), indinavir (IDV) nelfinavir (NFV), amprenavir (APV) and ABT-378.

The options for antiretroviral therapy have improved considerably as new agents have become available. Current guidelines for antiretroviral therapy recommend a triple combination therapy regimen for initial treatment, such as one PI and 2 NRTIs or one NNRTI and 2 NRTIs. These combination regimens show potent antiretroviral activity and are referred to as HAART (highly active antiviral therapy). The introduction of HAART has resulted in a significant reduction of morbidity and mortality in HIV-1 patient populations with access to these drugs.

Additionally, the development and standardization of plasma HIV-1 RNA quantification assays has led to the use of viral load measurements as a key therapy response monitoring tool. Viral load levels in pre- or minimally treated patients is a strong predictive factor for long-term disease progression and treatment-induced reductions in viral load have been associated with clinical benefit. The goal of antiretroviral therapy is to reduce plasma viremia to below the limit of detection on a long-term basis. This is partially achievable with standard HAART. However, in a significant number of patients, maximal suppression of virus replication is not achieved and for those in whom this goal is reached, a significant number experience viral load rebound. Although a rebound in plasma viremia is a clear indication of therapy failure, viral load data provides no information on the cause of the failure.

Why therapies fail may be due to a number of factors. These include insufficient antiviral activity of the regimen, individual variations in drug metabolism and pharmacodynamics, difficulties in adhering to dosing regimen, requirements for treatment interruption due to toxicity, and viral drug resistance. Moreover, drug resistance may develop in a patient treated with sub-optimal antiretroviral therapy or a patient may be infected with drug-resistant HIV-1. Although drug resistance may not be the primary reason for therapy failure, in many cases any situation which permits viral replication in the presence of an inhibitor sets the stage for selection of resistant variants.

More specifically, retroviruses such as HIV have no proof-reading mechanisms when synthesizing new nucleic acids strands. Errors that occur in the process of incorporating nucleotides during chain elongation are not corrected. This allows for the continuous generation of a number of genetic variants in a replicating viral population. The estimates are that there are $3 \times 10^{-5}$ mutations per nucleotides per HIV replication cycle and the type of substitution mutation is of course random at any one location. Consequently, given the frequency of the errors and the high rate at which the virus replicates, virtually all possible genetic changes are likely to be generated within a very short time period. More importantly, the genetic changes may alter the configuration of the RT and protease molecules in such a way that they are no longer susceptible to inhibition by the compounds that have been developed to target them. If antiretroviral therapy is ongoing and if viral replication cannot be completely suppressed, the selection of such genetic variants is inevitable. The viral population will become resistant to the drug(s)

administered. Clearly, effective suppression of the viral population is vital to effective treatment.

Viral drug resistance can be defined as any change in the virus that improves replication in the presence of an inhibitor. HIV-1 drug resistance was first described in 1989 and involved patients that had been treated with zidovudine monotherapy, which represented the only treatment option at that time. See Larder, B. A., et al., *Science* 243, 1731-1734 (1989). Resistance was detected phenotypically in vitro: for a number of patients, the viral isolates required 100-fold higher zidovudine concentrations to inhibit replication to the same extent as pretreatment isolates from the same individual. Subsequently, the genetic basis for zidovudine resistance was characterized.

Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the compounds used.

Resistance development has also been observed with the introduction of dual NRTI combination therapy as well as during the administering of the more potent NNRTIs and PIs. Individual antiretroviral agents differ in the rate at which resistance develops: selection for resistant variants may occur within weeks of treatment or resistance may emerge after a longer treatment period. The degree of susceptibility may encompass the whole range from slight reduction in susceptibility to complete resistance, depending on the type of mutation(s) harbored by the virus and the type and concentration of compound used.

Extensive genetic analysis of resistant viral isolates generated through in vivo or in vitro selection has revealed that resistance is generally caused by mutations altering the nucleotide sequence at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled. See Schinazi, R. F., Larder, B. A. & Meliors, J. W. 1997. *Int. Antiviral News.* 5, 129-142 (1997). Additionally, an electronic listing with mutations has also become available on the internet at sites such as hiv-web.lanl.gov or www.viralresistance.com.

It should be noted that the degree of susceptibility of a genetic variant to an antiretroviral compound is expressed herein relative to the wild-type virus (HIV III/B/LAI reference sequence) as found, for example, in GenBank, the sequence of which is hereby incorporated by reference. Susceptibilities are generally expressed as ratios of $IC_{50}$ or $IC_{90}$ values (the $IC_{50}$ or $IC_{90}$ value being the drug concentration at which 50% or 90% respectively of the viral population is inhibited from replicating). Additionally, the genetic mutation is normally written as in reference to the wild type virus, i.e., K101N refers to replacement of a Lysine at codon 101 with a Asparagine. However, the mutations of the invention do not depend on the wild-type example listed in order to be within the practice of the invention. For example, the mutation 101N, refers to an Asparagine at the 101 codon regardless of the whether there was a Lysine at 101 prior to mutation.

Of course, as antiretroviral drugs are administered for longer periods of time, mostly in combination with each other, and as new antiretrovirals are being developed and added to the present drugs, new resistance-correlated genetic variants are being discovered. Of particular import is that the combination of antiretroviral agents can influence resistance characteristics. For example, different NNRTI resistance-correlated mutations were selected on NNRTI-zidovudine combination therapy and different NRTI resistance-correlated mutations were selected in dual NRTI combination therapy. In the latter case, the result is high-level multi-drug resistance to all NRTIs. Alterations in susceptibility may also be towards sensitivity rather than resistance during dual combination therapy as shown by the reversal of ZDV resistance in patients treated with ZDV/3TC. In this case, the effect is mediated through the mutational interaction between M184V and ZDV-resistance substitutions. In patients on dual combination therapy, the time to resistance may be affected as shown for ZDV-resistance in ZDV/3TC or ZDV/NNRTI combinations. Studies also demonstrated that resistance to one of the agents in the combination (in these cases, lamivudine or the NNRTI) may appear more consistently/frequently than resistance to the other (here, zidovudine).

Moreover, once viral resistance has developed, salvage therapy options may be severely restricted due to cross-resistance within each drug class. Based on models of virus replication dynamics and mutation rates discussed above, it would appear that a shift to mutant (resistant) virus population under conditions of incomplete suppression of viral replication in the presence of inhibitors is only a matter of time. Thus, a key factor in preventing resistance is maintaining complete (maximal) suppression of virus replication.

In view of the prevalence of viral resistance and its role in therapy failure, prevention of resistance development must be a key goal in the management of antiretroviral therapies. Recently, interest has been focused on the characterization of alterations in viral drug susceptibility for better clinical management. Given the significant role played by the existence and the continued evolution of resistance to antiretroviral drugs, the right choice for treatment regimen is very important. This is as important for initial treatment as for when a therapy change is called for in order to minimize the emergence of resistance and improve the long-term prognosis of the patient. The choice of therapy regimen will be supported by knowledge of the resistance profile of the circulating virus population. Additionally, therapy combinations will have a greater chance of being effective if they include agents that have a demonstrated potential of suppressing a particular virus population. Thus, unnecessary side effects and costs associated with drugs that the patient's virus is resistant to, may be avoided. However, to date, the understanding of the correlation between mutations of HIV and drug resistance and the effect of multi-drug combinations on resistance characteristics to individual agents is insufficient to accomplish many of these goals.

To achieve these and other advantages, and in accordance with the purpose of the invention as embodied and broadly described herein, the present invention, in one aspect, provides a computer system comprising a database correlating the presence of at least one mutation in an HIV reverse transcriptase and the resistance of at least one strain of HIV to a reverse transcriptase inhibitor (RTI); and/or a database correlating the presence of at least one mutation in an HIV protease and the resistance of at least one strain of HIV to a protease inhibitor (PI). More specifically, the database comprises a set of records corresponding to a correlation between a mutation and drug resistance.

The correlations of the present invention between a mutation and drug resistance are: if the HIV reverse transcriptase mutation is 88E, 101H, 101N, 101P, 101Q, 101T, 103H, 103S, 179I, 179E, 181V, 190E, 190S, 190T or the combination of 103R and 179D, or any combination of these mutations, the strain of HIV is resistant to at least one NNRTI; if the HIV reverse transcriptase mutation is 69S-[S-S], 184G, 184L, 215 V, 44D, 44A, or 118I, or any combination thereof, the strain of HIV is resistant to at least one NRTI; and if the protease mutation is 88T and/or the combination of mutations 33F and 90M, or any combination thereof, the strain of HIV is resistant to at least one PI.

In another embodiment, the invention is drawn to a method of evaluating the effectiveness of antiretroviral therapy of an HIV-infected patient comprising: collecting a sample from an HIV-infected patient; determining whether the sample comprises at least one nucleic acid encoding HIV reverse transcriptase having at least one mutation described herein or HIV protease having at least one mutation described herein; and using the presence of the nucleic acid to evaluate the effectiveness of the antiviral therapy.

In a further embodiment, the invention provides for a method of identifying drugs effective against NNRTI or NRTI resistant strains of HIV, the method comprising the steps of: providing at least one strain of HIV comprising HIV reverse transcriptase containing at least one mutation described herein, determining the phenotypic response of the drug to the strain of HIV, and using the phenotypic response to determine the effectiveness of the drug. In an even further embodiment, the invention provides a method of identifying drugs effective against PI resistant strains of HIV, wherein the strain of HIV comprises HIV protease containing at least one mutation described herein, determining the phenotypic response of said drug to said strain of HIV, and using the phenotypic response to determine the effectiveness of the drug. In another embodiment, the invention provides for the drug identified using the methods of the invention.

The invention also provides for a method of designing therapy for treating patients infected with HIV comprising: collecting a sample from an HIV-infected patient; determining whether the sample comprises at least one nucleic acid encoding HIV reverse transcriptase having at least one mutation described herein or HIV protease having at least one mutation described herein; and using the presence of the nucleic acid to design a therapy for the patient.

The invention also includes isolated HIV reverse transcriptase complexes resistant to at least one NNRTI or at least one NRTI comprising at least one mutation described above and an isolated HIV protease complex resistant to a PI comprising at least one mutation described above.

Additional objects and advantages of the invention will be set forth in part in the description that follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE DRAWINGS

FIG. 2: Nucleoside analogue susceptibility of MDR patient-derived recombinant HIV variants. Recombinant viruses were produced from patient plasma samples as described in Example 2 and tested for susceptibility to (a) d4T, (b) ddC and (c) ddI. The mean fold increase in $IC_{50}$ values (Mean fold resistance) relative to wild-type controls are shown for groups of viruses with different genotypes, i.e., the codon 151-M multi-drug resistance cluster (n=27), viruses with 69D/N (n=195), or 75M (n=43) in a background of AZT and 3TC resistance mutations and codon 69 insertion mutants (n=45) in a background of AZT resistance mutations. Error bars indicate standard errors. Note that the total number (n=310) is higher than the 302 MDR samples described because a small minority were 69D/N and 75M double mutants and are represented in both groups.

DETAILED DESCRIPTION OF THE INVENTION

Figure 1:
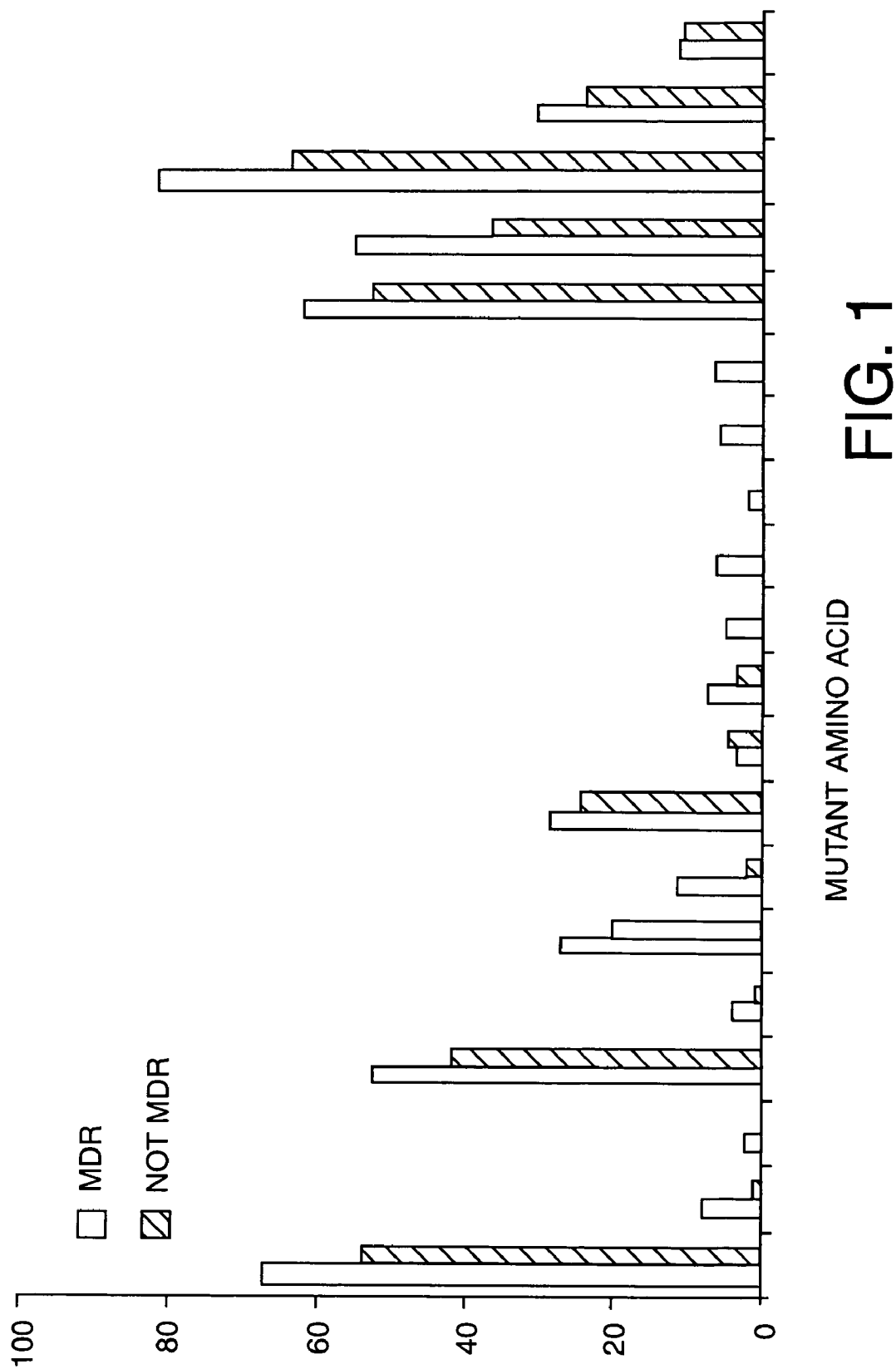
FIG. 1: Frequency of mutations in RT from multi-nucleoside resistant and nonMDR clinical samples. The clear bars (MDR) represent the overall frequency of RT mutations found in HIV-1 samples that had a >4-fold increase in $IC_{50}$ value to at least four of the nucleoside analogues tested. The striped bars (not MDR) show the mutation frequency of isolates that were not cross-resistant to four or more of the nucleosides. The individual mutations analyzed in this population of 892 samples are indicated in the single letter amino acid code. 69+ indicates amino acid insertions at codon 69.

Reference will now be made in detail to the presently preferred embodiments of the invention. The invention, in one aspect, provides novel mutations or mutational profiles of HIV-1 reverse transcriptase and/or protease genes correlated with phenotypic resistance to anti-HIV drugs. More particularly, the present invention also relates to the use of genotypic characterization of a target population of HIV and the subsequent correlation of this information to phenotypic interpretation in order to correlate virus mutational profiles with drug resistance. The invention also relates to methods of utilizing the mutational profiles of the invention in databases, drug development, i.e., drug design, and drug modification, therapy and treatment design, clinical management and diagnostic analysis.

Not to be limited as to theory, the invention utilizes a combinational approach involving genotypic and phenotypic resistance testing to correlate mutations with resistance phenotypes. Without the specific combination of the technologies mentioned above, this correlation between mutation and resistance would not have been detected. In addition to the observation of these genotypic and phenotypic profiles in isolates from routine clinical practice, site-directed mutants were generated to confirm that these mutations actually form the basis of this pattern of drug resistance.

Resistance of HIV to antiretroviral drugs may be determined at the genotypic level by identifying mutations in the HIV-1 genome and by inferring the resistance of HIV-1 to antiretroviral drugs through searching for mutational patterns known to correlate with resistance. Alternatively, resistance of HIV to antiretroviral drugs may be determined at the phenotypic level by culturing the virus in the presence of the inhibitors, and by measuring to what extent the drug inhibits viral replication. In this case, one measures the effect of all mutational interactions, the effects of genetic changes as yet unknown or not previously identified, the effect of the background genotype, etc., on the phenotype.

Assays for detection of mutations in HIV-1 are based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., *AIDS* 5, 137-144 (1991); Richman, D. D., et al., *J. Infect. Dis.* 164, 1075-1081 (1991); Gingeras, T. R., et al., *J. Infect. Dis.* 164, 1066-1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., *J. Acq. Imm. Def. Syndr. Human Retrovirol.* 9, 264-273 (1995); Holodniy, M., et al., *J. Virol.* 69, 3510-3516 (1995); Eastman, P. S., et al., *J. Clin. Micro.* 33, 2777-2780 (1995).); Line Probe Assay (LiPA™ HIV-11 RT, Innogenetics) (Stuyver, L., et al., *Antimicrob. Agents Chemotherap.* 41, 284-291 (1997).); and GeneChip technology (Affymetrix) (D'Aquila, R. T. *Clin. Diagnost. Virol.* 3, 299-316 (1995); Fodor, S. P. A. et al., *Nature* 364, 555-556 (1993); Fodor, S. P. A. *Nature* 227, 393-395 (1997). DNA sequencing assays, on the other hand, provides information on all nucleotides of the sequenced region. Target sequences are amplified by PCR. Sequence analysis is primarily based on the incorporation of dideoxy chain-terminating nucleotides (lacking 3' hydroxyl groups) in elongating DNA sequences and gel-electrophoretic analysis of the resulting molecules. Most sequencing technologies are semi-automated and make use of fluorescently labeled primers or ddNTPs to "read" off the sequence from a polyacrylamide gel.

Phenotyping assays measure the ability of a replicating virus to grow in the presence of specific inhibitors compared to a wild-type sensitive reference virus. Consequently, these assays directly measure the degree of viral resistance or susceptibility to specific inhibitors. Applicable phenotyping assays include but are not limited to: the PBMC (peripheral blood mononuclear cells) p24 Antigen Assay, which was the first standardized assay for determination of viral drug resistance in clinical HIV-1 isolates (Japour, A. J., et al., *Antimicrob. Agents Chemother.* 37, 1095-1101 (1993); Kusumi, K. et al., *J. Virol.* 66, 875-885 (1992); and the Recombinant Virus Assays (RVAs) which was first described as an alternative means of assessing phenotypic resistance to RT-inhibitors (Kellam, P. & Larder, B. A., *Antimicrob. Agents Chemother.* 38, 23-30 (1994); Hertogs, K., et al, *5th International Workshop on HIV Drug Resistance*, Whistler, Canada. Abstr. 64 (1996); Hertogs, K., et al., *Antimicrob. Agents Chemother.* 42, 269-276 (1998); Hertogs, K., et al., *International Workshop on HIV Drug Resistance, Treatment Strategies and Eradication*, St. Petersburg, Fla., USA. Abstr. 43 (1997); and Pauwels, R., et al., *2nd International Workshop on HIV Drug Resistance and Treatment Strategies*, Lake Maggiore, Italy. Abstr. 51 (1998).

As is the case with the genotyping assays, the recombinant virus assay starts with the amplification of viral target sequences by means of PCR. The amplicons are incorporated into a proviral laboratory clone with sequences homologous to those present in the amplicon deleted. This generates a stock of chimeric viruses. The viruses are tested for their ability to grow in the presence of different concentrations of drugs. Results are obtained by calculating $IC_{50}$ values for each inhibitor and by reporting the results as $IC_{50}$ values, expressed in µM concentrations, or by computing the ratio of the $IC_{50}$ values found for the chimeric virus to the $IC_{50}$ values found for a wild type susceptible laboratory virus tested in parallel. In the latter case, resistance is expressed as "fold-resistance" compared to a wild-type susceptible HIV-1 strain.

In order to meet the need for high-volume testing and a short turn-around time for an individual test, the latest generation of phenotyping assays has undergone further modifications. The use of reporter gene systems for susceptibility testing allows the implementation of laboratory automation and standardization. See Pauwels, et al., *J. Virol. Methods* 20, 309-321 (1998); Paulous, S., et al., *International Workshop on HIV Drug Resistance, Treatment Strategies and Eradication*, St. Petersburg, Fla., USA. Abstr. 46 (1997); and Deeks, S. G., et al., *2nd International Workshop on HIV Drug Resistance and Treatment Strategies*, Lake Maggiore, Italy. Abstr. 53 (1998).

Additionally, there are also assays that allow simultaneous testing of protease and reverse transcriptase susceptibility on a large scale. The Antivirogram™ assay (Virco) (WO 97/27480) is based on homologous recombination of patient derived HIV-1 gag/PR/RT sequences into a proviral HIV-1 clone correspondingly deleted for the gag/PR/RT sequences. See Pauwels, et al., *J. Virol. Methods* 20, 309-321 (1998). The resulting replication-competent recombinant viruses are analyzed in a reporter gene-based cellular assay in the presence of various concentrations of antiretroviral drugs. HIV-1 specific reporter-gene signals are generated as a result of viral replication in the target cells. Automated high-resolution optics are used to monitor ongoing viral replication at the single cell level. All currently available HIV-1 protease and reverse transcriptase inhibitors are analyzed in a single-microtitre plate susceptibility assay. A similar assay (ViroLogic) is based on enzymatic ligation of patient-derived PR/RT sequences into a correspondingly deleted proviral vector carrying an indicator gene, luciferase, inserted in the deleted HIV-1 envelope gene. See Deeks, S. G., et al., *2nd International Workshop on HIV Drug Resistance and Treatment Strategies*, Lake Maggiore, Italy. Abstr. 53 (1998). More information regarding these techniques may also be found in Hertogs et al. *Recent Res. Dev. Antimicrob. Agents Chemother,* 3(Pt 1) 83-104 (1999); Hertogs et al. *Antimicrob. Agents Chemother.* 44(3) 568-573 (2000); and Larder et al. *Antimicrob. Agents Chemother.,* 43(8) 1961-1967 (1999), the disclosures of which are herein incorporated by reference.

To summarize, the development of high-throughput phenotyping and genotyping assays has allowed the establishment of a database containing the phenotypic resistance data and the genotypic sequences of over 30,000 clinical isolates. Correlative data analysis and mutational cluster analysis of the database enables a search for mutational patterns with accompanying resistance.

Table 1 below lists the most commonly occurring resistance-correlated mutations appearing in clinical isolates after treatment with antiretroviral drugs.

TABLE 1

Examples of commonly occurring resistance-correlated mutations appearing in clinical isolates after treatment with antiretroviral drugs.

Protease Inhibitors

| | | |
|---|---|---|
| Primary Mutations: | D30N | Nelfinavir |
| | M46L, V82A | Indinavir |
| | G48V, L90M | Saquinavir |
| | V82A | Ritonavir |
| | I50V | Amprenavir |

TABLE 1-continued

Examples of commonly occurring resistance-correlated mutations appearing in clinical isolates after treatment with antiretroviral drugs.

| | |
|---|---|
| Secondary Mutations: | L10I/F/R/V, K20R/M, L24I, V32I, L33F, M36I, M46I, I47V, I54V/L, L63P, A71V/T, G73S, V77I, V82A/F/T/S, 184V, N88D, L90M |
| Compensatory Mutations: | In a PI-resistant mutational background, mutations at gag cleavage site(s) may partially restore viral replicative efficiency |
| Reverse Transcriptase Inhibitors | |
| NRTI Mutations: | M41L, K65R, D67N, T69D, K70R, L74V, V75T/M, M184V, L210W, T215Y/F, K219Q/E |
| MDR Mutations: | A62V, V75I, F77L, F116Y, Q151 M T69S with associated insertions of 1 to 3 amino acids between codons 68 and 70 of RT |
| NNRTI Mutations: | A98G, L100I, K101E, K103N/T, V106A, V108I, V179D/E, Y181 C/I, Y188C/L/H, G190A, P225H, P236L |
| Reversal Mutations: | M184I/V decreases the effect of zidovudine resistance mutations M41 L and T215Y. L74V decreases the effect of zidovudine resistance mutation T215Y. K65R in mutational background (D67N, K70R, T215Y and K219Q) decreases zidovudine resistance. Y181C decreases the effect of zidovudine resistance mutation T215Y. |

The invention contemplates resistance-correlated mutations to any type of HIV treatment therapy including but not limited to mutations conferring resistance to Protease Inhibitors and Reverse Transcriptase Inhibitors (NRTIs, NtRTIs, and NNRTIs) in addition to Multi-Drug Resistant Mutations.

In one embodiment, the invention contemplates mutations conferring resistance to Protease Inhibitors (PIs). Table 1 lists two categories of mutations for all PIs: primary and secondary mutations. Primary mutations may be the major contributor to the development of resistance to a particular drug. Secondary mutations appear either later during the course of therapy and also lead to resistance, or are already present as natural polymorphisms in a PI-naive viral isolate. A great number of secondary mutations enhance resistance to several PI-inhibitors simultaneously. This may lead to broad cross-resistance to this class of inhibitors, although subtle different phenotypic effects of those secondary mutations may exist.

Not to be limited as to theory, mutations occurring in the protease gene may impair cleaving efficiency of the polyprotein by the protease. Compensatory mutations have been found at the gag cleavage sites that allow more efficient cleaving of the sites by proteases that have mutated. Several studies of clinical isolates from protease-treated patients who have acquired PI resistance-correlated mutations have shown mutations at gag p7/p1 and/or p1/p6 sites significantly raised the replicative efficiency of the mutant viruses.

Other mutations within the practice of the invention may confer resistance to NRTIs and NNRTIs. For example, the mutations typically conferring resistance to the NRTI zidovudine are M41L, D67N, K70R, L21ØW, T215Y and K219Q. Multiple mutations in HIV-1 reverse transcriptase also may confer high-level resistance to zidovudine and other NRTIs. Multiple mutations, when present, may act synergistically, and susceptibility decreases as the number of resistance-correlated mutations increases. For example, mutations correlated with resistance to didanosine are L74V, K65R. Resistance to lamivudine is also correlated with the emergence of mutations M184V and M184I that confer very high resistance levels in addition to low-level resistance to didanosine, and zalcitabine. A low-level resistance to lamivudine may also be present in the absence of the 184 mutation while resistance to abacavir is correlated with mutations K65R, L74V, Y115F and M184V.

Another embodiment of the invention relates to multi-drug resistance mutations (MDR) and particularly MDRs to NRTIs. For example, the RT mutational constellation A62V, V75T, F77L, F116Y and Q151M together causes resistance to all nucleoside analogues.

Mutations conferring resistance to Non-Nucleoside Reverse Transcriptase inhibitor (NNRTIs) are also contemplated by the invention. For example, resistance-correlated mutations for nevirapine are A98G, L100I, K103N, V106A, V108I, Y181C/I, Y188C and G190A. These mutations are K103/N/T, Y181C and P236L for delavirdine and for resistance to efavirenz, the mutations are L100I, K101E, K103N, V108I, V179D. Y181C and Y188L.

Another aspect of the invention concerns reversal mutations. For example, the M184V lamivudine resistance mutation decreases the effect of zidovudine resistance mutations M41L and T215Y, while the L74V didanosine resistance mutation decreases the effect of zidovudine resistance mutation T215Y. Whether the described reversal effects are phenotypically significant or not, however, may depend on the combinations of mutations that are present.

In another embodiment, mutations may increase sensitivity to inhibitors. For example, the delavirdine mutation, P236L increases sensitivity of this mutant to inhibition by nevirapine and the lamivudine-resistance mutation M184V causes increased susceptibility to adefovir and to PMPA above the non-mutant sequence. This increased sensitivity seems to be reflected in an enhanced treatment outcome.

Novel mutations of HIV-1 reverse transcriptase (Table 2a) and protease (Table 2b) within the practice of the invention, and their correlated phenotypic drug resistance, include but are not limited to those shown in Table 2.

TABLE 2a

Novel RT Mutations and the Correlated Drug Resistance

| Reverse Transcriptase Mutation | Resistant to: |
|---|---|
| 88E | NNRTI |
| K101H | NNRTI |
| K101N | NNRTI |
| K101P | NNRTI |
| K101Q | NNRTI |
| K101T | NNRTI |
| K103H | NNRTI |
| K103S | NNRTI |
| K103S + K101P | NNRTI |
| K103R + K179D | NNRTI |
| V179I | NNRTI |
| V179E | NNRTI |
| Y181V | NNRTI |
| G190E | NNRTI |
| G190S | NNRTI |
| G190T | NNRTI |
| 44D | NRTI |
| 44A | NRTI |
| 118I | NRTI |
| M184G | NRTI |
| M184L | NRTI |
| 215V | NRTI |

Table 2b: Novel Protease Mutations and the Correlated Drug Resistance

TABLE 2b

Novel Protease Mutations and the Correlated Drug Resistance

| Protease Mutation | Resistant to: |
|---|---|
| 33F + 90M | PI |
| 88T | PI |

The existence of a single mutation or any combination of the mutations in Table 1 may confer resistance to one or more treatments from the correlated class. For example, mutations 88E, K101H, K101N, K101P, K101Q, K101T, K103H, K103S, K103S+K101P, K103R+K179D, V179I, V179E, Y181V, G190E, G190S, and G190T are MDRs and confer resistance to multiple NNRTIs, while mutations M184G and M184L have only been found to confer resistance to 3TC, and mutation 215V has only been found to confer resistance to AZT. Likewise, the protease mutation at 88T confers resistance to nelfinavir, while the combination of protease mutations, 33F+90M confers resistance to amprenavir. However, if the appropriate tools are utilized, such as those described herein, e.g., the Vircogen, one may take the identified mutation and the correlated-resistance to a class of treatment, as provided by Table 2, and screen for other applicable treatments within the specified. Therefore, the invention also provides that the listed mutations and new combination of mutations, armed with the correlated class of drug, can be used to predict new resistance phenotypes such as resistance to additional PIs, NRTIs, NNRTIs, or MDR resistance. Additionally, the existence of a combination of mutations may confer the same or a different drug resistance profile.

The invention also provides other novel mutations and/or combinational mutations and their correlated drug resistance. In particular, one object of the present invention is the mutations E44D, E44A and V118I. Each mutation independently may be capable of generating resistance to an NRTI (3TC).

In another embodiment, the invention provides a correlation between any combination of two or more of the HIV RT mutations E44D, E44A, V118I and/or M184V and resistance to one or more NRTIs, and more specifically to ZDV and/or 3TC. Formerly, only a methionine to valine or isoleucine mutation at position 184 of HIV reverse transcriptase has been correlated with significant phenotypic resistance to an NRTI (lamivudine). In a further embodiment, one or more of the mutations E44D, E44A, and V118I in combination with one or more of the mutations 41L, 67N, 69D, 70R, 210W, 211K, 214F, 215Y, 215F, 219Q and 219E may confer resistance to one or more NRTIs, and more specifically to ZDV and/or 3TC.

Another aspect of the invention is a group of MDR mutations with one, two or three amino acid insertions and/or rearrangements between codons 67 and 70 of RT, with the insertions preferably being 69S-[S-S] or 69S-[S-G]. These patterns of mutations may be correlated with high-level phenotypic multi-nucleoside or multi-drug resistance. The codon 69 insertion mutants may be alone or in combination with other mutations. Other preferred mutations and/or rearrangements between codons 67 and 70 of RT are shown in Table 3. (The resistance data for several of these mutations and combinations is shown in Table 4.) These mutations also may confer resistance alone or in combination with other mutations.

In another embodiment, mutations and/or rearrangements between codons 67 and 70 of RT confer resistance (MDR) in combination with one or more of the mutations 62V, 210W, and/or 215Y.

TABLE 3

Spectrum of genetic heterogeneity seen between RT codons 67 and 70 in clinical samples containing amino acid insertions.

| Amino Acid Sequence | | | | | | | n |
|---|---|---|---|---|---|---|---|
| D67 | S68 | T69 | X | X | | K70 | |
| D | S | S | — | — | | K/R | 4 |
| G | Y | T | D | — | | R | 1 |
| D/E | S | S | S | S | | K/R | 16 |
| D/E | S/N | S | S | G | | K | 10 |
| D/E | S | S | E | E | | K | 3 |
| D/E | S/N | S | S | A | | K | 3 |
| D/E | S | S | V | G | | K/R | 2 |
| D | S | S | A | G | | K | 1 |
| D | S | A | S | G | | K | 1 |
| D67 | S68 | X | X | X | T69 | K70 | |
| D/E | S | S | V | — | T | K | 2 |
| D | S | S | T | — | T | K | 1 |
| D/E | S | S | S | — | T | K | 3 |
| S | S | S | S | G | T/A | — | 1 |
| G | S | G | G | G | T | — | 1 |

Wild-type amino acid residues are shown in the main headings and amino acid insertions are marked as an 'X'. Samples having only the substitution of Thr69Ser are also shown. Alternative amino acid residues are shown at various positions for different samples, or where mixed nucleotides were detected within a single sample. Positions where no amino acid was seen are indicated by a dash (—).

TABLE 4

Nucleoside analogue susceptibility of HIV-1 variants constructed by site-directed mutagenesis.

| Mutant genotype | Fold increase in $IC_{50}$ | | | | | |
|---|---|---|---|---|---|---|
| | d4T | AZT | 3TC | 1592 | ddI | ddC |
| 69S-[S-S] | 2.3 | 2.2 | 6.2 | 2.6 | 1.7 | 2.1 |
| 210W, 215Y | 1.1 | 10 | 3.8 | 1.5 | 1.2 | 1.2 |
| 210W, 215Y, 62V | 0.7 | 8 | 1.3 | 0.7 | 0.5 | 0.8 |
| 69S-[S-S], 210W, 215Y | 4.8 | 220 | 20 | 4.6 | 2.1 | 4.2 |
| 69S-[S-S], 210W, 215Y, 62V | 5.2 | >2500 | 15 | 5.4 | 1.8 | 2.7 |

Mutations were created in HIV-1 RT by site-directed mutagenesis and the mutant RT was then transferred into the HXB2-D wild-type virus background. The specific mutations created in this background are indicated. The nucleoside susceptibility of mutant viruses (fold increase in $IC_{50}$ value relative to wild-type HXB2-D virus control) was assessed as described in 'Methods'. These data represent the mean values of two independent determinations. The mean $IC_{50}$ values for the wild-type control virus in these experiments were as follows: AZT, 0.04 μM, d4T, 2.39 μM, 3TC, 1.67 μM, ddI, 4.6 μM, ddC, 1.41 μM and 1592U89, 2.9 μM.

The present invention is also drawn to methods of using the correlations of the invention. In one embodiment, the invention provides for a database comprising the correlation between: the presence of at least one mutation in HIV reverse transcriptase and the resistance of at least one strain of HIV to a reverse transcriptase inhibitor (RTI); or the presence of at least one mutation in HIV protease and the resistance of at least one strain of HIV to a protease inhibitor (PI).

In a further embodiment, the database may assist a physician in developing a treatment program or in determining the appropriate HIV therapy or combination therapy. For example, the VircoGEN™ genotypic assay system is a diagnostic tool for monitoring HIV-1 drug resistance. The system can be used for studying resistance development in clinical trials of anti-HIV-1 drugs, for improved clinical management of HIV-1 infected patients and for studying epidemiological aspects of drug resistance. It allows for a rapid determination of the drug sensitivity of the HIV-1 population circulating in the plasma of patients who have been exposed to antiretroviral drugs or who have been infected with drug resistant HIV-1 strains.

The invention also provides for a method of monitoring HIV-1 drug resistance using a method such as the one used in the VircoGEN™, which combines in one test the determination of the genetic sequence of patient-derived HIV-1 genetic material and the interpretation of sequence variations found in the patient HIV strain with respect to the possible existence of antiviral drug resistance. In one embodiment, mutations associated with resistance to the different nucleoside reverse transcriptase inhibitors zidovudine, (AZT), didanosine (ddI), zalcitabine (ddC), stavudine (d4T), lamivudine (3TC) and abacavir, the nucleotide reverse transcriptase inhibitor adefovir (PMEA), the non-nucleoside reverse transcriptase inhibitors nevirapine, delavirdine and efavirenz, and the protease inhibitors saquinavir, ritonavir, indinavir and nelfinavir, are evaluated. The interpretation of the genotype may be based on lists of drug resistance-associated mutations published in peer-reviewed journals.

The methods of monitoring HIV-1 drug resistance, may also be used in combination with phenotypic drug resistance testing of viral isolates. For example, in one embodiment, a phenotypic test is utilized that is based upon the construction of chimaeric HIV-1 strains composed of the protease (PR) and reverse transcriptase (RT) gene sequences which are isolated and amplified from the patient viral RNA. These strains may subsequently be recombined inside CD4+ T cells with a standard laboratory isogenic (HXB2) HIV-1 DNA construct from which the PR/RT gene sequences were deleted. The recombinant strains may then be grown in the presence of the above-mentioned antiviral drugs and the susceptibility of the viral isolates may be expressed as fold-change value of the IC50 of the drug on the patient isolates over the IC50 of the drug on a wild-type laboratory reference strain.

In one embodiment, the sample to be tested is prepared from a patient and the genotypic assay is performed through automated population-based full-sequence analysis (ABI). Therefore, the sequencing method used may provide information on all nucleotides of the sequenced region. Sequencing results may be reported as amino acid changes at positions in the protease gene and the reverse transcriptase gene compared to the wild-type reference sequence. The changes included in the genotyping report may be limited to mutations at positions known to manifest drug resistance-associated polymorphisms. Polymorphisms at positions not associated with drug resistance are not required.

In an even further embodiment, a report may be generated that shows the region of the patient virus that has been sequenced, the mutations detected by the test, and/or an interpretation of the evidence obtained. The interpretation may include the antiretroviral drugs, the drug(s) for which a known resistance-associated mutation has been identified and/or to what extent the observed mutations are indicative of resistance to the drugs.

Knowledge of correlated geno- and phenotypes, together with knowledge of the catalytic site on the viral target for new compounds may also be utilized to tailor the construction of new molecules and the implementation of new (combination) treatments for HIV.

In another embodiment, the invention is drawn to a method of evaluating the effectiveness of antiretroviral therapy of an HIV-infected patient comprising: collecting a sample from an HIV-infected patient; and determining whether the sample comprises at least one nucleic acid encoding HIV reverse transcriptase having at least one mutation or HIV protease having at least one mutation. The sample may be a plasma sample, blood cells, or other tissue. Further, the invention has the potential to ameliorate HIV genotypic resistance diagnostics and can, in principle, lead to a better therapy and, under certain conditions, even be life saving.

In a further embodiment, the invention provides for a method of identifying or designing drugs effective against NNRTI or NRTI resistant HIV, the method comprising the steps of: providing at least one strain of HIV comprising a nucleic acid encoding HIV reverse transcriptase containing at least one mutation, and determining the phenotypic response of the HIV strain to a drug. In an even further embodiment, the invention provides a method of identifying drugs effective against PI resistant strains of HIV, wherein the strain of HIV comprises HIV protease containing at least one mutation, and determining the phenotypic response of said strain of HIV to said drug. The invention is also useful for interpretation of resistance of HIV isolates. It can also be used in full sequence analysis of HIV. In addition, the invention has applications for hybridization-based HIV analyses or in drug design, development, testing and marketing. In a further embodiment, the invention includes the drugs designed by the methods of the invention.

The invention also provides for a method of designing therapy for treating patients infected with HIV comprising correlating the presence of HIV reverse transcriptase having at least one mutation described above with resistance to at least one NNRTI or at least one NRTI, or correlating the presence of HIV protease having at least one mutation with resistance to at least one PI.

The identification of the comparative mutations of the invention may lead to improved antiretroviral drug treatment programs. As outlined above, there is ample evidence demonstrating that poor virologic response to drug therapy may be correlated with the existence of genotypic and/or phenotypic viral resistance to one, several, or in the worst case, all available antiretroviral drugs. As a consequence, resistance testing using the correlations of the invention may be used as a tool for identifying those drugs that no longer contribute towards decreasing the plasma viral load.

EXAMPLES

Example 1

The Identification of Novel Mutational Patterns in HIV-1 Reverse Transcriptase and the Correlated Phenotypic Resistance Plasma samples were obtained from HIV-1-infected individuals from routine clinical practice in Europe and the US and were shipped to the laboratory on dry ice and stored at −70° C. until analysis.

Phenotypic analysis was performed using the recombinant virus assay. See Kellam, P., and B. A. Larder. *Antimicrob Agents Chemother* 38:23-30 (1994); Hertogs, K., et al., *Agents Chemother.* 42:269-276 (1998); Pauwels, R., et al., *Abstracts of the 2nd International Workshop on HIV Drug Resistance and Treatment Strategies*, Abstr. 51. Lake Maggiore, Italy (1998). Briefly, protease (PR) and reverse transcriptase (RT) coding sequences were amplified from patient-derived viral RNA with HIV-1 specific primers. After homologous recombination of amplicons into a PR-RT deleted proviral clone, the resulting recombinant viruses were harvested, titrated and used for in vitro susceptibility testing to antiretroviral drugs. The results of this analysis were expressed as fold-resistance values, reflecting the fold-increase in mean $IC_{50}$ (μM) of a particular drug when tested with patient-derived recombinant virus isolates, relative to the mean $IC_{50}$ (μM) of the same drug obtained when tested with a reference wild-type virus isolate (IIIB/LAI).

Genotypic analysis was performed by automated population-based full-sequence analysis (ABI). Results of the genotypic analysis are reported as amino acid changes at positions along the reverse transcriptase gene compared to the wild-type (HXB2) reference sequence. Cluster analysis by VircoGEN™ interpretational software (Virco Ltd, Cambridge, UK) allowed detection of the occurrence of mutational pattern in the database containing the genetic sequences of the clinical isolates and linkage with the corresponding resistance profiles of the same isolates. See Pauwels, R., et al. *2nd International Workshop on HIV Drug Resistance and Treatment Strategies*, Lake Maggiore, Italy. Abstr. 51 (1998).

For the modeling studies, mutations were generated in the RT gene of HXB2, a wild-type laboratory HIV-1 strain, using the QuikChange™ Site-Directed Mutagenesis Kit, Stratagene, Stratagene Cloning systems, La Jolla, Calif., USA.

Analysis of the Clinical Isolates

Table 5 reports the frequency of mutations 44D/A, 118I, 184V, 215Y, and 41L in RT in clinical isolates with various levels of phenotypic resistance to zidovudine (ZDV) and lamivudine (3TC). The mutant isolates described here were drawn from a pool of clinical isolates.

TABLE 5

Frequency of ZDV and 3TC Resistance-correlated Mutations in Clinical Isolates Susceptible or Resistant to ZDV and/or 3TC Compared to a Sample of Fully Susceptible Isolates

| | Frequency (%) of mutations | | | | | |
|---|---|---|---|---|---|---|
| | ZDV resistance-correlated mutations | | 3TC resistance-correlated mutations | | | |
| Resistance Class[a] | 41L | 215Y | 184V | 44D/A | 118I | No. of samples |
| ZDV (<4), 3TC (<4) | 4.5 | 4.8 | 0 | 1.3 | 3.1 | 314 |
| ZDV (<4), 3TC (>10) | 18.3 | 18.8 | 90 | 1.3 | 6.3 | 240 |
| ZDV (>10), 3TC (<4) | 59.5 | 68.9 | 0 | 14.9 | 18.9 | 74 |
| ZDV (>10), 3TC (≧4, <50) | 77 | 72.2 | 4 | 30.2 | 39.7 | 126 |
| ZDV (>10), 3TC (≧50) | 77.5 | 66.9 | 84.1 | 28.5 | 37.8 | 151 |

[a]Resistance (in parentheses) is expressed as the fold increase in the mean $IC_{50}$ of the drug relative to the mean $IC_{50}$ of the same drug for a wild-type reference laboratory HIV-1 strain.

Isolates that are susceptible (WT) to both ZDV and 3TC (n=195): the frequency of any of the six mutations listed above was low.

Isolates that are resistant to ZDV (>10-fold, n=220): Table 5 shows that the ZDV resistance-correlated mutations 215Y, 41L and 70R were high in frequency in this category and throughout all 3TC resistance categories. Mutation 184V was the predominant mutation in the high-resistance 3TC class (>50-fold), whereas 184V was rare in the intermediate 3TC resistance group and absent in the low-level resistance group and the 3TC susceptible group. The mutations 44D/A and 118I were present in all 3TC resistance categories.

Isolates that are resistant to 3TC (>10-fold, n=295): Table 5 shows that the frequency of the high-level 3TC resistance-correlated mutation, 184V, was high in all ZDV resistance categories (low, intermediate and high) and was the predominant mutation in the ZDV susceptible and intermediate-resistance group. As the resistance to ZDV increased, so did the frequency of the ZDV resistance-correlated mutations 41L, 70R and 215Y, while the frequency of mutation 184V decreased. Mutations 44D/A and 118I also substantially increased in frequency as resistance to ZDV increased.

The results thus far show that low and intermediate resistance to 3TC was not related to the presence of mutation 184V. Indeed, this mutation was practically absent in these classes. Table 5 further indicates that mutations 44D/A and 118I were present in high frequencies only in the presence of ZDV resistance mutations 215Y, 41L and 70R. In the isolates that were susceptible to ZDV, the frequency of ZDV resistance-correlated mutations was low and 44A/D and 118I were also rare, even though 3TC resistance was greater than 10-fold. In this group the high frequency of 184V accounted for the resistance to 3TC.

Analysis of the Mutants Generated by Site-Directed Mutagenesis

Table 6 shows the codon changes introduced into a wild-type HXB2 background together with the fold-resistance values obtained when the different mutants were tested in the drug susceptibility assay. All six mutants carrying mutation 184V were highly resistant to 3TC. Two of them carried both 44D/A and 118I, while all but one (SDM23) carried ZDV resistance-correlated mutations.

TABLE 6

3TC and ZDV resistance-correlated mutations and phenotypic resistance in mutants with site-directed mutations

| | | 3TC resistance profile | | AZT resistance profile | | |
|---|---|---|---|---|---|---|
| Mutant | Mutation(s) | Fold resistance[a] | n[b] | Mutations | Fold resistance | n |
| SDM05 | | 4 (0.3)[c] | 4 | 41L, 210W, 211K, 214F, 215Y | 64 (15.0) | 5 |
| SDM18 | | 2 (0.6) | 3 | 41L, 67N, 210W, 211K, 214F, 215Y | 45 (13.4) | 3 |
| SDM19 | | 4 (0.7) | 3 | 41L, 67N, 69D, 210W, 211K, 214F, 215Y | 46 (18.2) | 2 |
| SDM28 | 44D | 1 (0.1) | 6 | | 2 (0.3) | 6 |
| SDM31 | 44D | 22 (2.5) | 5 | 41L, 67N, 210W, 211K, 214F, 215Y | 48 (11.8) | 4 |
| SDM32 | 44D | 8 (2.2) | 4 | 41L, 67N, 69D, 210W, 211K, 214F, 215Y | 49 (5.9) | 6 |
| SDM29 | 118I | 2 (0.2) | 6 | | 2 (0.4) | 6 |
| SDM33 | 118I | 7 (1.0) | 5 | 41L, 67N, 210W, 211K, 214F, 215Y | 49 (8.0) | 6 |
| SDM34 | 118I | 32 (3.9) | 5 | 41L, 67N, 69D, 210W, 211K, 214F, 215Y | 34 (14.4) | 5 |
| SDM30 | 44D, 118I | 3 (0.3) | 6 | | 1 (0.4) | 6 |

TABLE 6-continued

3TC and ZDV resistance-correlated mutations and phenotypic resistance in mutants with site-directed mutations

| | | 3TC resistance profile | | AZT resistance profile | | |
|---|---|---|---|---|---|---|
| Mutant | Mutation(s) | Fold resistance[a] | n[b] | Mutations | Fold resistance | n |
| SDM35 | 44D, 118I | 14 (1.4) | 6 | 41L, 67N, 210W, 211K, 214F, 215Y | 49 (9.6) | 5 |
| SDM36 | 44D, 118I | 15 (2.1) | 6 | 41L, 67N, 69D, 210W, 211K, 214D, 215Y | 49 (10.6) | 5 |
| SDM22 | 184V | 78 (16.3) | 5 | 41L, 210W, 211K, 214F, 215Y | 7 (0.9) | 5 |
| SDM23 | 184V | 82 (13.6) | 6 | | 2 (0.5) | 6 |
| SDM24 | 184V | 85 (14.2) | 6 | 69S-S-S, 210W, 211K, 214D, 215Y | 27 (16.2) | 5 |
| SDM26 | 184V | 72 (13.8) | 5 | 41L, 67N, 210W, 211K, 214F, 215Y | 25 (1.4) | 5 |
| SDM38 | 184V, 44D, 118I | 82 (13.5) | 6 | 41L, 67N, 210W, 211K, 214F, 215Y | 20 (4.1) | 6 |
| SDM39 | 184V, 44D, 118I | 84 (13.9) | 6 | 41L, 67N, 69D, 210W, 211K, 214F, 215Y | 21 (5.3) | 5 |

[a] Fold increase in the mean $IC_{50}$ of the drug relative to the mean $IC_{50}$ of the same drug for a wild-type reference laboratory HIV-1 strain.
[b] n, number of replicate tests run for each phenotype drug resistance determination.
[c] Standard errors are indicated in parentheses.

All of the mutants followed the predicted ZDV resistance or susceptibility pattern. At the same time, three mutants were generated with a change at codon 44, three with a change at codon 118 and three with a change at both codons 44 and 118. Within each of these three groups two mutants also carried changes at positions correlated with resistance to ZDV, whereas one mutant remained wild-type at those codons. The drug resistance values listed in Table 6 clearly show that the presence of mutations at codon 44 and 118, singly or together, can cause intermediate resistance to 3TC (8 to 32-fold), distinguishable from the high resistance to 3TC (>62-fold) caused by mutation 184V. Moreover, the intermediate resistance to 3TC was only observed when mutations at positions 44 and/or 118 occurred in a ZDV-resistant background (41L, 67N, 210W, 215Y) while resistance caused by mutation 184V was obviously not related to ZDV resistance.

Relationship Between the Presence of Changes at RT Positions 44 or 118 in Clinical Samples and Antiretroviral Therapy As can be deduced from Table 6, changes at position 44 and 118 may occur in virus samples with or without the M184V substitution, but they appeared at higher incidence in samples with ZDV resistance. It was therefore of interest to look at the antiretroviral treatments administered to patients with HIV-isolates that contained 44D or 118I. We identified a subset of 86 samples with 44D and 88 samples with 118I originating from patients for whom antiretroviral histories were available. Although it was not possible to draw conclusions regarding the incidence of changes at 44 or 118 from this subset according to treatment history, as this was not a randomized study, this analysis nevertheless shed some light on the conditions that may lead to mutations at these positions.

For the 44D subset, 50/86 of the samples originated from patients who were receiving lamivudine at the sample date and 5 patients in this subset had never received 3TC prior and up to the sample date. All 5 patients had received zidovudine/didanosine at some time and all HIV-isolates were wild-type at position 184. The zidovudine treatment experience was extensive, as expected for historical reasons. All except one patient had received zidovudine in combination with other NRTI's and 70/86 had also received zidovudine monotherapy in the past. The one patient reported to be zidovudine naive had received stavudine. This sample contained 41L and 215Y.

Results for 118I subset were similar in that 55/88 samples originated from patients who were on lamivudine at the sample date and 2 patients had never received lamivudine (both had received zidovudine plus didanosine). Most patients, 83/88, had received zidovudine in combination with other NRTI's, and 70 had also received zidovudine monotherapy. The 5/88 zidovudine naive patients had received stavudine. For a few patients, consecutive samples showing the evolution of 44D or 118I were available.

These results indicate that mutations E44D/A and V181I in HIV-1 RT confer a low to intermediate level of resistance to 3TC when they occur in clinical isolates possessing a ZDV-resistant background. The cluster analysis of genotypically and phenotypically characterized clinical isolates and the results from the site-directed mutagenesis experiment confirm that indeed mutations at codons 44 and 118 are correlated with low and intermediate level of resistance to 3TC, with the restriction that ZDV resistance-correlated mutations be present. Additionally, the analysis of the clinical samples for which therapy histories were available and in which prior ZDV exposure was shown to be extensive, confirmed the results obtained from our large clinical data set in that mutations 44D/A and 118I appeared in the context of ZDV mutations.

Mutations 44D/A and 118I each are capable of independently generating resistance to 3TC. The experiment with site-directed mutagenesis does not indicate the existence of synergistic effects between the two mutants with respect to their phenotypic effect on 3TC resistance.

Example 2

Determining the Genetic Basis of HIV-1 Multi-Nucleoside Resistance

This study was designed to investigate the occurrence of HIV-1 multi-nucleoside resistance in a relatively large number of clinical samples and to determine the genetic basis of this resistance. 892 HIV-1 samples were surveyed in our resistance database from patients failing therapy using a standardized recombinant-based phenotypic assay and by DNA sequence analysis. Multi-nucleoside resistance was correlated with complex mutational patterns in the RT coding region.

Plasma samples were obtained from patients who had received antiretroviral therapy. Selection was on the basis of a viral load >1000 HIV-1 RNA copies/ml and for the purpose of this study, patients with this level of plasma HIV-1 were considered to be failing therapy.

Viral RNA was extracted from 200 μl patient plasma using the QIAamp Viral RNA Extraction Kit (Qiagen, Hilden, Germany), according to the manufacturers instructions. cDNA encompassing part of the pol gene was produced using Expand™ reverse transcriptase (Boehringer Mannheim) as described previously. See Hertogs K., et al., *Antimicrob. Agents Chemother.* 42: 269-276 (1998). A 2.2 kb fragment encoding the protease and RT regions was then amplified by nested polymerase chain reaction (PCR) using PCR primers and conditions as described. Id. This genetic material was subsequently used in both phenotyping and genotyping experiments.

MT-4 cells (Harada S., et al, *Science* 229: 563-566 (1985).) were co-transfected with pol gene PCR fragments and the protease-RT deleted HIV-1 molecular clone, pGEM3ΔPRT, as described. See Hertogs K., et al., *Antimicrob. Agents Chemother.* 42: 269-276 (1998). This resulted in viable recombinant viruses containing protease/RT from the donor PCR fragment. Phenotypic susceptibility to nucleoside analogues was determined using an MT-4 cell viral cytopathic effect (CPE) protection assay as described. Id. Fold resistance values were derived by dividing the mean $IC_{50}$ for a patient's recombinant virus by the mean $IC_{50}$ for wild-type control virus (strain HXB2-D).

The PCR products obtained from patient plasma samples were genotyped by dideoxynucleotide-based sequence analysis. Samples were sequenced using the Big Dye terminator kit (Applied Biosystems) and resolved on an ABI 377 DNA sequencer.

Mutations in the RT coding region were created by site-directed mutagenesis of a wild-type HXB2-D EcoRI-PstI restriction enzyme fragment, encompassing the HIV-1 pol gene and cloned into pGEM3 (Promega). Single and multiple nucleotide changes were introduced into RT using the ExSite mutagenesis kit (Strategene). All mutant clones were verified by DNA sequence analysis of the entire RT. PCR fragments were prepared from the mutated clones and the altered RT coding regions were transferred into the HIV-1 HXB2-D genetic background by homologous recombination as described above. The susceptibility of these recombinant viruses to nucleoside analogues was subsequently determined by the MT-4 cell CPE protection assay. Id.

Phenotypic Susceptibility Analysis

The recombinant virus assay (Antivirogram™) was used to determine simultaneously the susceptibility of the samples to AZT, 3TC, d4T ddI and ddC. From this analysis, 302 samples were identified with four-fold or greater increases in $IC_{50}$ (relative to a wild-type control virus) to at least four of these inhibitors. Thus, a substantial number of MDR viruses were present in the sample population.

Genotypic Analysis of Multi-Nucleoside Resistant Samples

Genotypic analysis was performed on all 892 samples by dideoxy-nucleotide sequencing. Complex patterns of multiple mutations were seen in the RT coding regions of the MDR samples. These included combinations of AZT and 3TC resistance mutations (particularly 41L, 67N, 210W and 215Y with 184V/I) plus mutations at codons 69 (T69A/N) and/or 75 (V75M). A comparison of the incidence of specific RT mutations in MDR samples versus non-MDR in the population surveyed is shown in FIG. 1. This analysis highlighted the incidence of the codon 151 mutational cluster in the MDR group. In addition, a novel family of amino acid insertions and rearrangements between codons 67 and 70 were also prevalent in the MDR group. These two patterns of mutations were correlated with high-level phenotypic multi-nucleoside resistance (FIG. 2), 27 samples having the codon 151 cluster and 45 samples having insertions and rearrangements (typically a T69S substitution, followed by insertion of two amino acids). The mean fold increases in $IC_{50}$ to d4T, ddI and ddC for these different groups are shown in FIG. 2. This analysis indicated that codon 69 insertion mutants had a high degree of d4T and ddC resistance (>10-fold), which was also seen with the codon 151 cluster. However, samples with AZT and 3TC resistance mutations plus T69A/N or V175M showed only modest levels of resistance to these drugs (FIG. 2). Not surprisingly, all four groups shown in FIG. 2 were highly resistant to AZT and 3TC (mean fold increase in AZT $IC_{50}$ of >500-fold and >30-fold for 3TC). This was because many MDR samples contained mutations conferring AZT resistance (e.g., 41L, 67N, 210W and 215Y) and 3TC resistance (Met184V/I).

Spectrum of Different Insertions Seen in the RT Codon 67 to 70 Region

The extensive variety of insertions in the, codon 67 to 70 region of RT is summarized in Table 3. The largest group (n=16) had a T69S substitution followed by insertion of two S residues. The next largest group (n=10) also had a T69S substitution but in this case a different insertion of S-G. Samples with a number of different double amino acids inserted after 69Ser were also identified. In addition, insertions of two or three amino acids between codons 68 and 69 were also seen. The positions of these insertions were based on the fact that T69 and L70 were contiguous. In some samples there were rarely observed substitutions at codon 67 (A67G/S/G), rather than the common 67N AZT resistance mutation. In two samples deletion of codon 70 was observed (after insertion of three residues between codons 68 and 69), and a single substitution of T69S without an insertion was seen in four samples (Table 3). The inserted residues did not show any obvious patterns in terms of codon usage. For example, the S-S insertions were rarely direct repeats of the S69 codon, suggesting that simple reiterations of S69 could not account for the appearance of these insertions in the RT.

Patients' Therapy Patterns in Relation to Codon 69 Insertions

Figure 3:
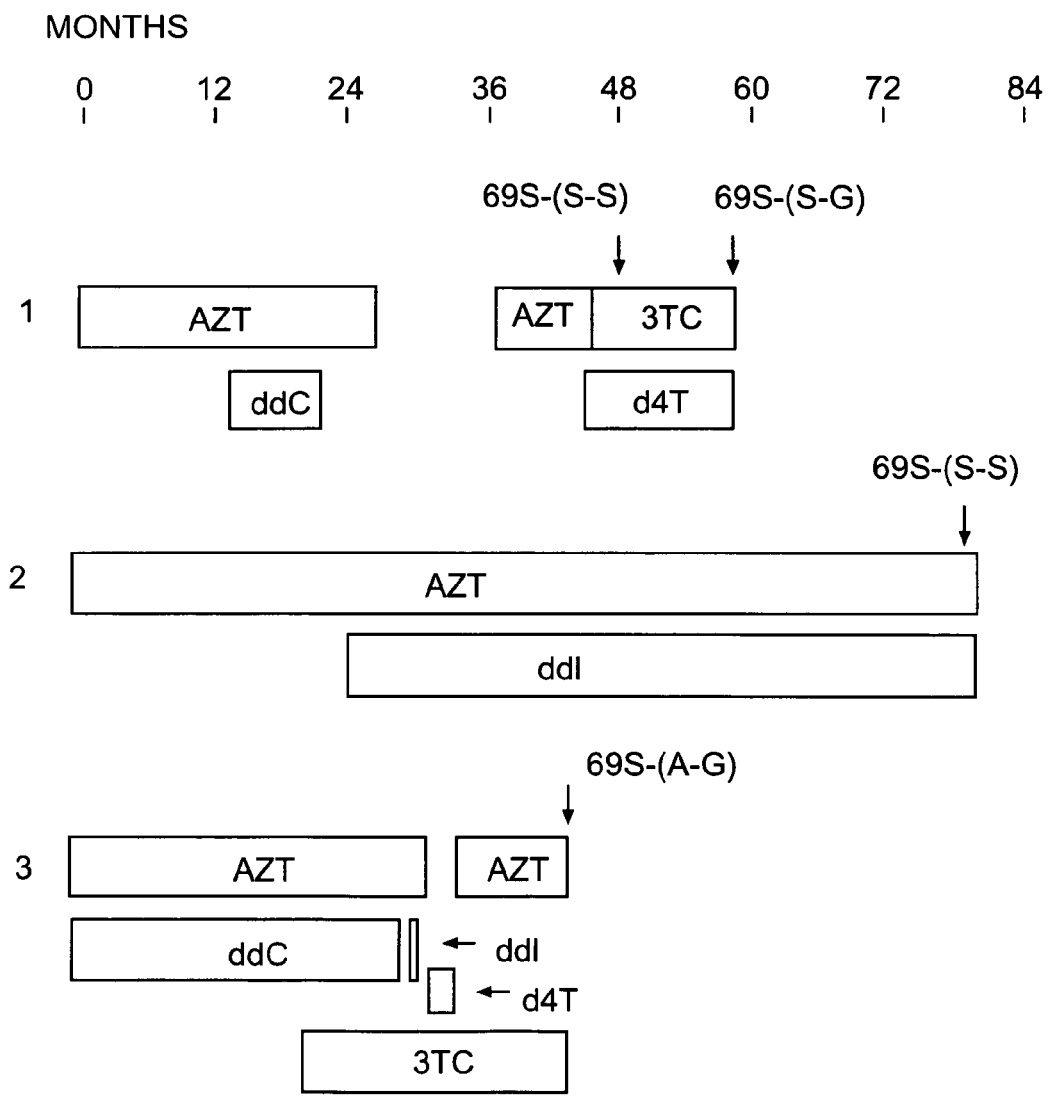
FIG. 3: Therapy histories of three patients whose HIV-1 isolates developed codon 69 insertions. Nucleoside analogue therapies (AZT, 3TC, ddC, ddI or d4T) are shown as horizontal bars, indicating the time period in which each patient (1, 2 or 3) received a particular treatment. The time point at which plasma samples were obtained for genotypic and phenotypic analysis are shown by the arrows together with the specific codon 69 insertion detected. Any other therapies besides nucleosides that these patients may have been receiving are not indicated on this figure.

The codon 69 insertions were always present in a background of AZT resistance mutations, especially T215Y/F. This may not be surprising as therapy histories from many of the patients whose samples were analyzed in this study revealed a common pattern of AZT therapy, followed by combination therapy with nucleosides and protease inhibitors (data not shown). FIG. 3 shows typical treatment patterns for three patients, indicating the time samples were obtained for virological analysis. It was not possible from these histories to determine precisely the nucleoside analog(s) responsible for selecting codon 69 insertions. Sequential samples from patient 1 revealed an interesting transition of 69S-[S-S] to 69S-[S-G] during a period of 3TC/d4T combination therapy.

Susceptibility Analysis of HIV-1 Variants Constructed by Site-Directed Mutagenesis To investigate the significance of the observed mutational patterns correlated with MDR virus we constructed a series of viruses by site-directed mutagenesis with specific changes in a defined genetic background (HXB2-D). T69A or V75M in a background of AZT mutations conferred little or no resistance to 3TC, d4T, ddI or ddC. Variants were also constructed with 69S-[S-S], either alone or together with two AZT resistance mutations (210W and 215Y). In addition, the potential role of A62V, a substitution also frequently correlated with the insertions was investigated by adding this mutation to a background of 69S-[S-S] plus 210W/215Y. Susceptibility data for six nucleoside analogues are summarized in Table 4. These data showed that the 69S-[S-S] insertion alone did not confer multi-nucleoside resistance. In fact, this virus only had a significant decrease in susceptibility to 3TC. By contrast, the variants with the insert plus AZT resistance mutations had decreased susceptibility to AZT, 3TC, d4T, ddC and abacavir (4-[(2-amino-6-cyclopropyl-amino)-9H-purin-9-yl]-2-cyclopentene-1-methanol, 1592U89), confirming that the 69 insertions plus AZT mutations conferred the MDR phenotype.

All references, patents, and patent applications cited herein are incorporated by reference in their entirety.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A method of evaluating the effectiveness of an HIV-1 antiviral therapy of an HIV-1 infected patient comprising:

(i) collecting a sample from an HIV-1 infected patient;

(ii) detecting in said sample each of the following nucleic acids:

a) a first nucleic acid encoding an HIV-1 reverse transcriptase comprising:

1) at least one mutation chosen from the group consisting of 88E, 101H, 101N, 101P, 101Q, 101T, 103H, 103S, 179I, 179E, 181V, 190E, 190S and 190T; or 2) a combination of mutations 103R and 179D, in which the presence of said first nucleic acid correlates with resistance to a Non-Nucleoside Reverse Transcriptase Inhibitor (NNRTI);

b) a second nucleic acid encoding an HIV-1 reverse transcriptase comprising at least one mutation chosen from the group consisting of 69S-[S-S], 184G, 215V, 44D, 44A, and 118I, in which the presence of said second nucleic acid correlates with resistance to a Nucleoside Reverse Transcriptase Inhibitor (NRTI); and c) a third nucleic acid encoding an HIV-1 protease comprising:

1) mutation 88T; or 2) a combination of mutations 33F and 90M, in which the presence of said third nucleic acid correlates with resistance to a Protease Inhibitor (PI);

whereby the presence of each of the nucleic acids in step (ii) individually correlates with the effectiveness of said HIV-1 antiviral therapy.

* * * * *